(12) United States Patent
Park

(10) Patent No.: US 6,408,443 B1
(45) Date of Patent: Jun. 25, 2002

(54) REVERSIBLE VISOR

(75) Inventor: Boo Yl Park, Seoul (KR)

(73) Assignee: Dada Corp., Seoul (KR)

( * ) Notice: Subject to any disclaimer, the term of this patent is extended or adjusted under 35 U.S.C. 154(b) by 0 days.

(21) Appl. No.: 09/836,328

(22) Filed: Apr. 18, 2001

(51) Int. Cl.⁷ ................................................. A42B 1/00
(52) U.S. Cl. ........................ 2/195.1; 2/195.6; 2/209.12; 2/DIG. 2
(58) Field of Search ................... 2/195.1, 183, 209.12, 2/175.5, 195.6, DIG. 2, 12

(56) References Cited

U.S. PATENT DOCUMENTS

| | | | | |
|---|---|---|---|---|
| 1,816,346 A | * | 7/1931 | Silverstein | 2/172 |
| 5,450,629 A | * | 9/1995 | Gilstrap | 2/10 |
| 5,572,745 A | * | 11/1996 | Mainus | 2/171.2 |
| 5,893,170 A | * | 4/1999 | Garza | 2/12 |
| 6,311,331 B1 | * | 11/2001 | Park | 2/175.1 |

* cited by examiner

*Primary Examiner*—Rodney M. Lindsey
(74) *Attorney, Agent, or Firm*—Jacobson Holman, PLLC

(57) ABSTRACT

A visor structure for hats and sun visors in which a visor material of a soft or rigid material is partially cut from the upper and lower ends at predetermined intervals to allow the cut visor to maintain its curved shape when bent along the cut lines so that when a cap or sun visor with a visor of this structure is turned inside out, the visor maintains its curved shape. By attaching a different letter or figure of a mark, emblem or logo on the inner and outer portions respectively of the main body, and by using different colored or textured fabric, a single hat or sun visor structure can display effectively two different hats or sun visors in one to satisfy the diversified preferences of the wearer.

17 Claims, 5 Drawing Sheets

REVERSIBLE VISOR

BACKGROUND OF THE INVENTION

1. Field of the Invention

The present invention relates to an improved visor structure for hats and sun visors and, more particularly to a visor structure that is partially cut at predetermined intervals for maintaining its curved shape. When a hat or sun visor with a visor of this structure is turned inside out the visor maintains its curved shape allowing a hat or sun visor to be fully reversed to provide an effect of two caps or sun visors in one.

2. Description of the Prior Art

Typically, when engaging in outdoor activities such as mountain climbing, traveling, or attending sporting events, headwear, such as baseball style caps, hats and sun visors are worn to protect the wearer's eyes and face from the exposure to direct sunlight. However, many persons find it desirable to own and wear headwear that is not only capable of providing protection from the sun, but headwear that is also varies in appearance, color, texture and design. Accordingly, a variety of headwear, easily changeable in design, color, texture and shape has been provided.

An example of such headwear includes U.S. Pat. No. 4,776,043 to Coleman. The patent discloses a single hat structure with interchangeable patches that can be selectively attached to carry a variety of different logos. U.S. Pat. No. 5,181,277 to Sherman discloses a reversible cap comprising two crown members that can be interchangeably reversed to display two different colors, team logos, indicia, etc. U.S. Pat. No. 4,606,077 to Phillips discloses a reversible sun visor comprising a bill portion formed of stretchable fabric and polymeric material that allows a sun visor to be used inside out.

However, the aforementioned reversible cap, hat and sun visor assemblies have shortcomings in that, to provide a reversible hat assembly that is easily reversed, materials of a soft and flexible nature have to be used. This limits the use of materials of a hard or rigid nature.

SUMMARY OF THE INVENTION

Therefore, it is an object of the present invention to provide an improved reversible hat or sun visor structure that overcomes the limitations of the prior art in which a soft and flexible visor material has to be used to allow reversal. By cutting a visor material at predetermined intervals and allowing the visor to maintain its curved shape, a general hat or sun visor with a cut visor attaches easily and maintains its natural curve shape, regardless of the visor material employed.

Another object of the present invention is to provide an improved hat or sun visor structure that employs a different colored or textured fabric on the inner and outer portions respectively of a hat or sun visor, and a different logo or emblem respectively attached to the inner and outer portions of the main body of a hat or sun visor to allow a single hat or visor structure to display effectively two different hats or sun visors in one by simply reversing the hat or sun visor structure.

To achieve these and other advantages and in accordance with the purpose of the invention, as embodied and broadly described, the invention provides a reversible sun visor. The sun visor includes a loop-shaped main body comprised of an outer fabric material, an inner fabric material, an upper periphery and a lower periphery. A thin and narrow fabric is stitched along the upper periphery of the main body to cover the unsightly tucks made by the fabric portions joined together. A cut visor is attached to the lower periphery of the main body. The cut visor includes a visor material having a fixed size and thickness for defining the cut visor. The visor material has inner and outer portions and is partially cut at predetermined intervals to leave an uncut portion to retain the visor material in one piece. The inner and outer portions of the visor material are covered with fabric pieces of same size and are stitched with a thin and narrow fabric along an outer periphery of the visor material. A size adjustable portion adjusts the size of the loop of the reversible sun visor and is a part of the loop-shaped main body.

In another aspect, the invention includes a reversible hat. The hat includes a main body comprised of a crown consisting of an outer fabric material and an inner fabric material. Each of the outer fabric material and the inner fabric material respectively consists of a plurality of fabric panels. The main body has a lower periphery. A cut visor is attached to the lower periphery of the main body. The cut visor includes a visor material having a fixed size and thickness for defining the cut visor. The visor material has inner and outer portions and is partially cut at predetermined intervals to leave an uncut portion to retain said visor material in one piece. The inner and outer portions of the visor material are covered with fabric pieces of same size and are stitched with a thin and narrow fabric along an outer periphery of the visor material. A size adjustable portion adjusts the size of the reversible hat and is attached to a predetermined portion of the main body.

DETAILED DESCRIPTION OF THE PREFERRED EMBODIMENT

Figure 1:
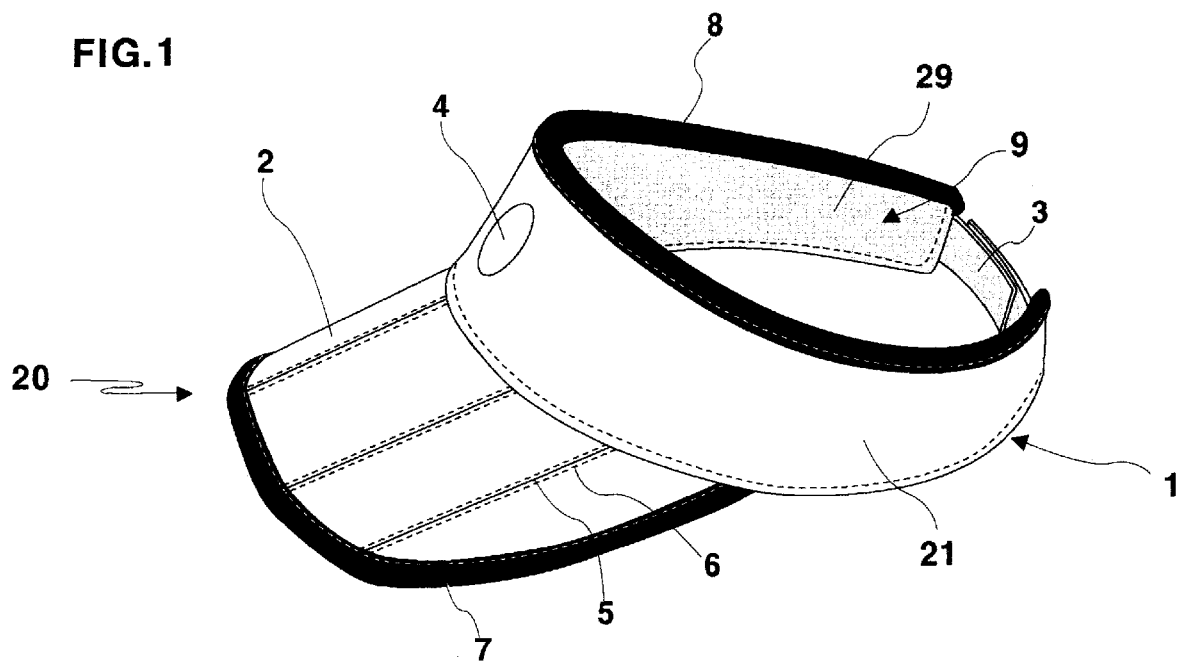
FIG. 1 is a perspective view of a sun visor of the present invention with a reversible visor.
Figure 2:
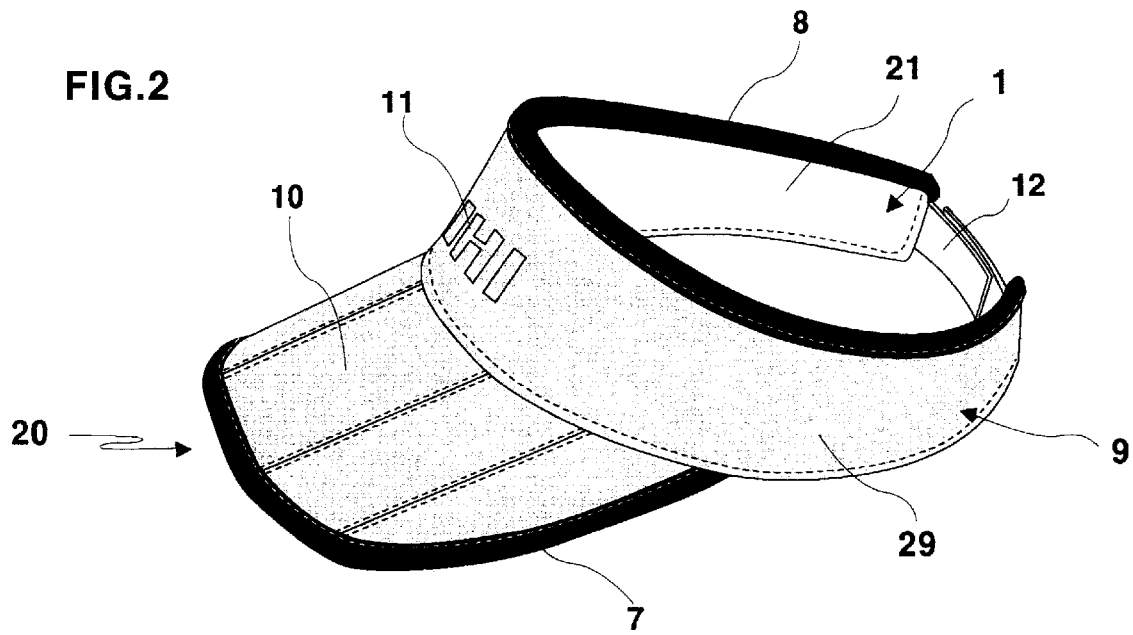
FIG. 2 is a perspective view of a sun visor of FIG. 1 in its reversed state.

In accordance with the preferred embodiment of the present invention, and with particular attention directed to FIGS. 1 and 2, a sun visor, generally indicated by numeral 20, includes a cut visor 2 attached and sewn to the front portion of the sun visor 20.

FIG. 1 is a perspective view of the sun visor 20 with a reversible visor. As illustrated in the drawing, the sun visor 20 of the preferred embodiment has a loop-shaped outer and inner main body, generally indicated by numerals 1,9. The cut visor 2 is attached and sewn to a lower periphery of the main body 1,9. A size adjustable portion 3 for adjusting the size of the sun visor to fit the wearer's head is sewn and attached to a portion of the main body 1,9, preferably to a back portion of the main body 1,9. The main body 1,9 of the sun visor 20 is formed of two layers of fabric, and a thin and narrow fabric 8 is stitched along the upper periphery of main body 1, 9 to cover the unsightly tucks made by the two layers of fabric joined together.

A personal or company logo, emblem, or mark 4 is embroidered on the front portion of the main body 1. The cut visor 2 forms cut visor lines 5 following the cuts at the predetermined intervals, and stitch lines 6 are formed along both sides of lines 5 to allow the curve shape of the visor 2 to be easily changed by the cut visor lines 5. A thin and narrow fabric 7 is stitched along the outer periphery of the visor 2 to stabilize the cut visor portions.

An inner fabric material 29 and an outer fabric material 21, comprising the main body 1,9 and the cut visor 2, are composed of different colored materials and can also be composed of different textured materials to achieve an effect of two sun visors in one. The inner fabric material 29 and the outer fabric material 21 can be stretchable fabric or non-stretchable fabric.

FIG. 2 is a perspective view of a sun visor of FIG. 1 in its reversed state. As illustrated in the drawing, when the main body 1,9 and the cut visor 2 of the sun visor of FIG. 1 is reversed, the inner portion of FIG. 1 becomes the outer portion of FIG. 2 and the outer portion of FIG. 1 becomes the inner portion of FIG. 2. The cut visor lines 5 make it possible for the sun visor to maintain its curved visor shape as in FIG. 1 even in its reversed state, and by producing a different personal or company logo, emblem, or mark 11 on the fabric material 29, an effect of two sun visors in one can be achieved.

Figure 3:
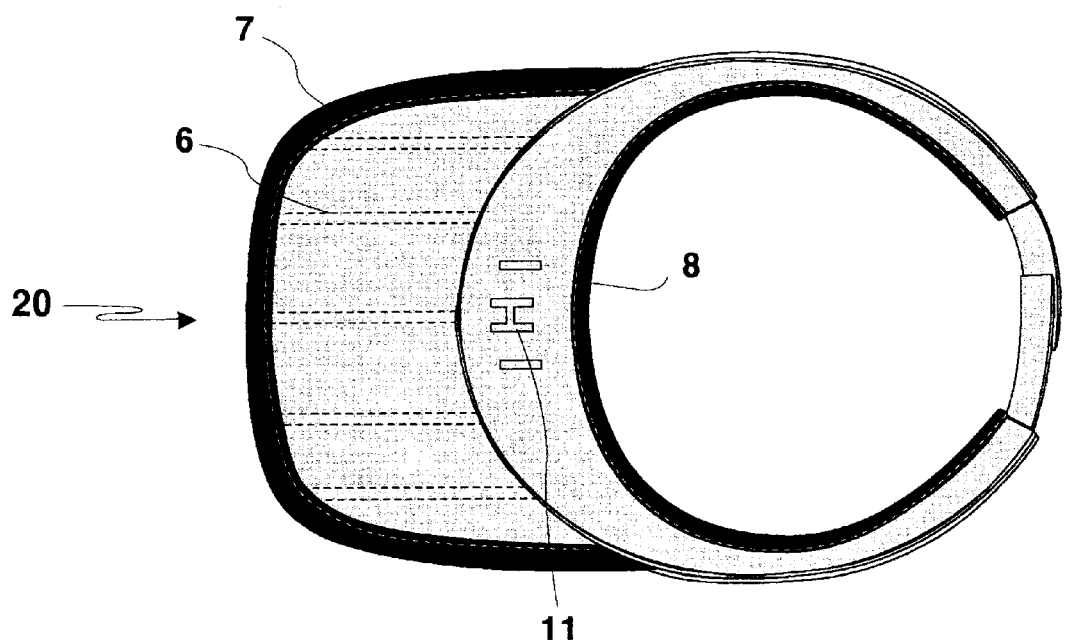
FIG. 3 is a bottom view of a sun visor of FIG. 1 with a reversible visor.

FIG. 3 is a bottom view of the sun visor of FIG. 1. As illustrated in the drawing, the inner fabric material 29 of the sun visor 20 is composed of a different color from the outer fabric material 21 and the inner portion of the main body has a different logo, emblem, or mark 11 than the outer portion. The inner portion of the cut visor 2 that is attached and sewn to the lower periphery of the main body 1,9 also has stitch lines 6 formed along the cut lines 5.

Figure 4:
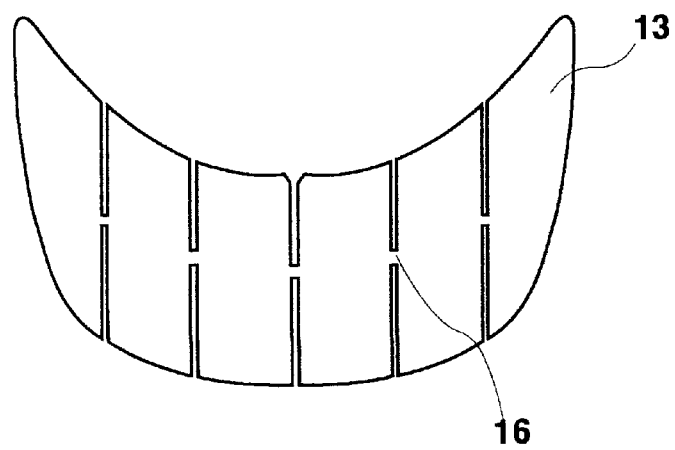
FIG. 4 is a top plan view of a visor portion of a reversible visor.

FIG. 4 is a plan view of the material forming the visor portion. As illustrated in the drawing, the visor material 13 is partially cut starting from the upper and lower ends respectively at predetermined intervals, and leaving an uncut portions 16 to retain the visor material 13 in one piece. The visor material can be composed of any kind of flexible, soft or rigid material.

Figure 5:
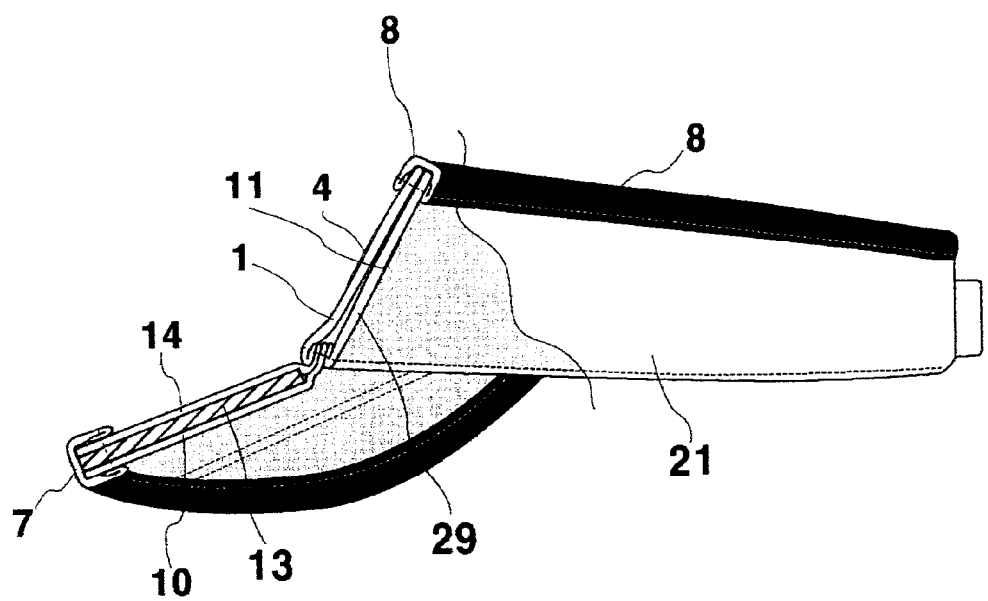
FIG. 5 is a cross-sectional view of the right side of a sun visor of FIG. 1.

FIG. 5 is a cross-sectional view of the right side of the sun visor 20 of FIG. 1. As illustrated in the drawing, the main body 1 of the sun visor 20 is composed of two layers of an inner fabric material 29 and an outer fabric material 21, and a thin and narrow fabric 8 is stitched along the upper periphery of main body 1, 9 to cover the unsightly tucks formed by the two layers of fabric being joined together. The cut visor 2 of the above sun visor is composed of a mutually different color and/or textured material on the inner portion 10 and the outer portion 14 with a soft or rigid visor material 13 in between. A thin and narrow fabric 7 is stitched along the lower periphery of the cut visor 2 to stabilize the cut visor portions.

The cut visor illustrated in the preferred embodiment of the present invention can also be attached and sewn to a general hat structure using the same method. Detailed description of the reversible hat is provided in connection with FIGS. 6–8. In this embodiment, the same visor material illustrated in FIG. 4 is also used.

Figure 6:
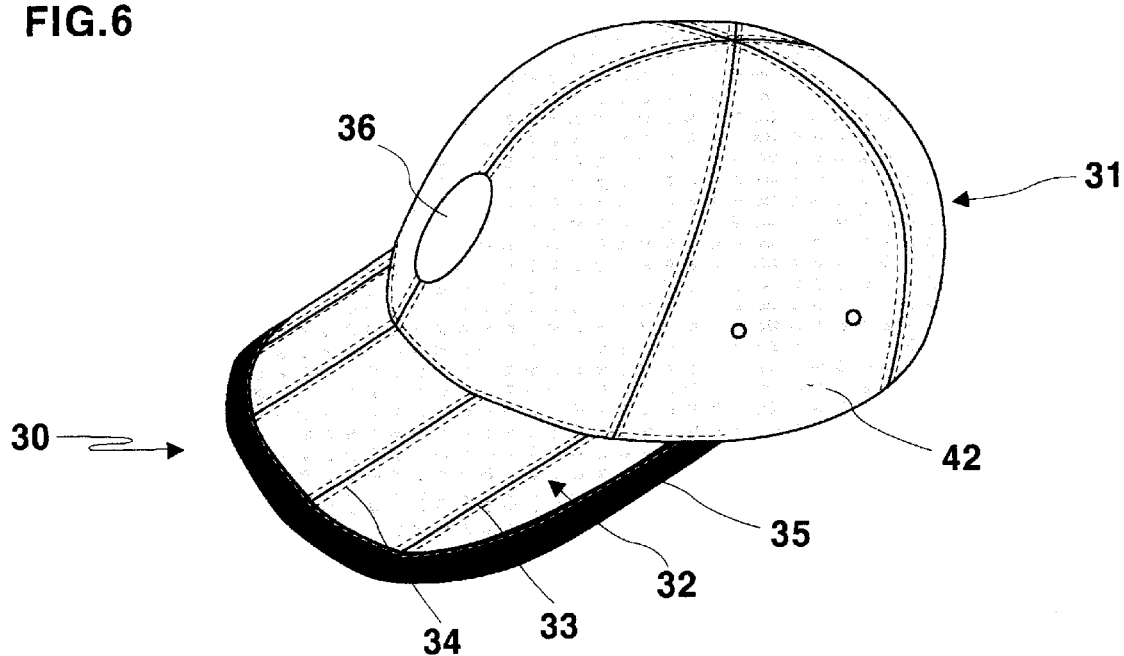
FIG. 6 is a perspective view of a reversible hat of the present invention with a reversible visor.

FIG. 6 is a perspective view of the reversible hat 30. As illustrated in the drawing, the hat 30 is comprised of an outer and inner main body, generally indicated by numerals 31, 39. A cut visor 32 is attached and sewn to a lower periphery of the main body 31, 39. The cut visor 32 is attached and sewn to a lower periphery of the main body 31, 39. A size adjustable portion 43 (shown in FIG. 8) for adjusting the size of the reversible hat 30 to fit the wearer's head is sewn and attached to a portion of the main body 31, 39, preferably to a back portion of the main body 31, 39. The main body 31, 39 of the reversible hat 30 is formed of two layers of fabric.

A personal or company logo, emblem, or mark 36 is embroidered on the front portion of the main body 31. The cut visor 32 forms cut visor lines 33 following the cuts at the predetermined intervals, and stitch lines 34 are formed along both sides of the cut visor lines 33 to allow the curve shape of the visor 32 to be easily changed by the cut visor lines 33. A thin and narrow fabric 35 is stitched along the outer periphery of the visor 32 to stabilize the cut visor portions.

An inner fabric material 40 (shown in FIG. 7) and an outer fabric material 42, comprising the main body 31, 39 and the visor 32, are composed of different colored materials and can also be composed of different textured materials to achieve an effect of two reversible hats in one. The inner fabric material 40 and the outer fabric material 42 can be stretchable fabric or non-stretchable fabric.

Figure 7:
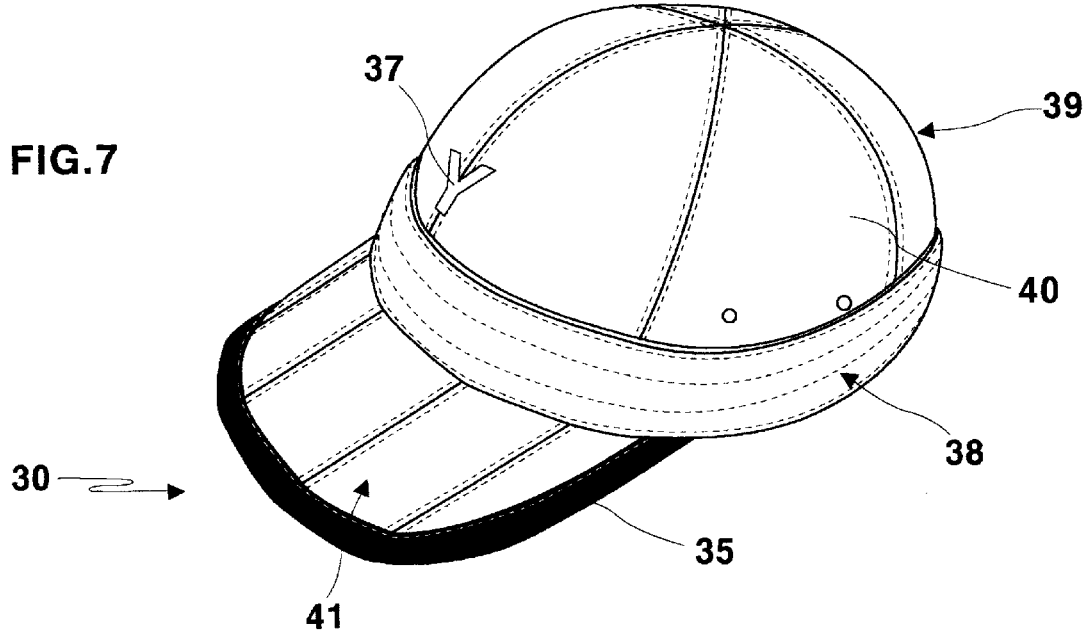
FIG. 7 is a perspective view of a reversible hat of FIG. 6 in its reversed state.

FIG. 7 is a perspective view of a reversible hat of FIG. 6 in its reversed state. As illustrated in the drawing, when the main body 31, 39 and the cut visor 32 of the sun visor of FIG. 6 is reversed, the inner portion of FIG. 6 becomes the outer portion of FIG. 7 and the outer portion of FIG. 6 becomes the inner portion of FIG. 7. The cut visor lines 33 make it possible for the sun visor to maintain its curved visor shape as in FIG. 6 even in its reversed state, and by producing a different personal or company logo, emblem, or mark 37 on the fabric material 40, an effect of two reversible hats in one can be achieved. In the reversed state, a band 38 is attached to a lower periphery of the inner fabric material 40. In the embodiment of FIG. 6, this band 38 (not shown in FIG. 6) is used as a sweat band.

Figure 8:
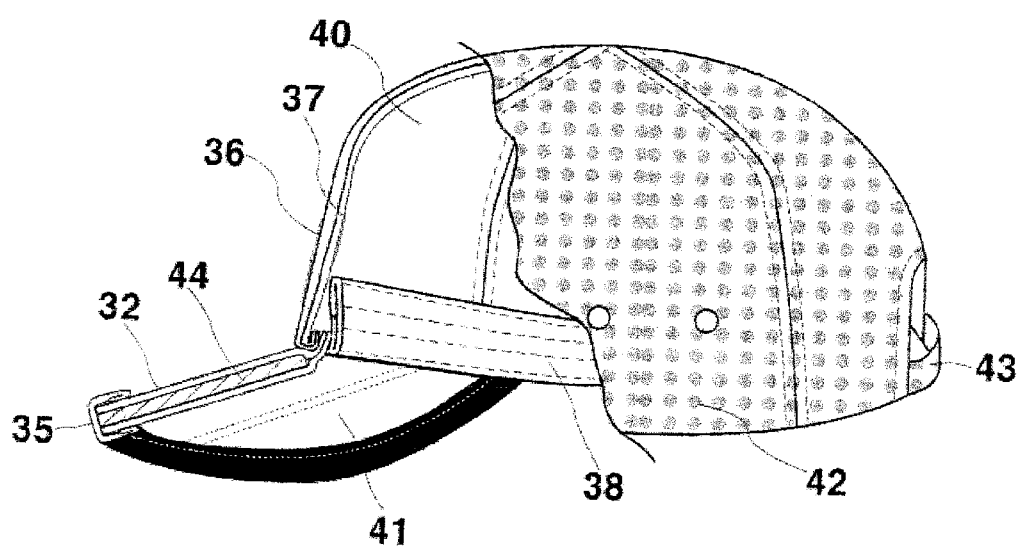
FIG. 8 is a cross-sectional view of the right side of the reversible hat of FIG. 6.

FIG. 8 is a cross-sectional view of the right side of the sun visor 30 of FIG. 6. As illustrated in the drawing, the main body of the reversible hat 30 is composed of two layers of an inner fabric material 40 and an outer fabric material 42. The cut visor 32 of the reversible hat 30 is composed of a mutually different color and/or textured material on the inner portion and the outer portion with a soft or rigid visor material 44 in between. A thin and narrow fabric 35 is stitched along the lower periphery of the visor 35 to stabilize the cut visor portions.

Although the invention herein has been described in accordance with particular embodiments, it is to be understood that these embodiments are merely illustrative of the principals and applications of the present invention and that numerous modifications and other arrangements may be devised without departing from the spirit and scope of the present invention as defined by the appended claims.

What is claimed is:

1. A reversible sun visor, comprising:
   a loop-shaped main body comprised of an outer fabric material, an inner fabric material, an upper periphery and a lower periphery;
   a thin and narrow fabric stitched along the upper periphery of said main body to cover unsightly tucks made by portions of the fabric materials joined together;
   a cut visor attached to the lower periphery of said main body, said visor comprising a visor material having a fixed size and thickness for defining said cut visor, the visor material having inner and outer portions and being partially cut at predetermined intervals to leave an uncut portion to retain said visor material in one piece, and the inner and outer portions of said visor material being covered with fabric pieces of same size and being stitched with a thin and narrow fabric along an outer periphery of the visor material; and a size adjustable portion for adjusting the size of the loop of the reversible sun visor and consisting a part of the loop-shaped main body.

2. The reversible sun visor according to claim 1, wherein said visor material is comprised of a flexible and soft material.

3. The reversible sun visor according to claim 1, wherein said visor material is comprised of a hard and rigid material.

4. The reversible sun visor according to claim 1, wherein said fabric materials are one of stretchable fabric or non-stretchable fabric.

5. The reversible sun visor according to claim 1, wherein said visor displays a different curve shape depending on the predetermined intervals.

6. The reversible sun visor according to claim 1, wherein the fabric pieces covering the inner and outer portions of said visor material are formed of different colored fabric.

7. The reversible sun visor according to claim 1, wherein the fabric pieces covering the inner and outer portions of said visor material are formed of different textured fabric.

8. The reversible sun visor according to claim 1, wherein the size adjustable portion is attached to a back portion of the main body.

9. A reversible hat, comprising:

a main body comprised of a crown consisting of an outer fabric material and an inner fabric material, each of the outer fabric material and the inner fabric material respectively consisting of a plurality of fabric panels, and said main body having a lower periphery;

a cut visor attached to the lower periphery of said main body, said cut visor comprising a visor material having a fixed size and thickness for defining said cut visor, the visor material having inner and outer portions and being partially cut at predetermined intervals to leave an uncut portion to retain said visor material in one piece, and the inner and outer portions of said visor material being covered with fabric pieces of same size and being stitched with a thin and narrow fabric along an outer periphery of the visor material; and a size adjustable portion for adjusting the size of the reversible hat and being attached to a predetermined portion of the main body.

10. The reversible hat according to claim 9, wherein said visor material is comprised of a flexible and soft material.

11. The reversible hat according to claim 9, wherein said visor material is comprised of a hard and rigid material.

12. The reversible hat according to claim 9, wherein said fabric panels are one of stretchable fabric or non-stretchable fabric.

13. The reversible hat according to claim 9, wherein said visor displays a different curve shape depending on the predetermined interval.

14. The reversible hat according to claim 9, wherein the fabric pieces covering the inner and outer portions of said visor material are formed of different colored fabric.

15. The reversible hat according to claim 9, wherein the fabric pieces covering the inner and outer portions of said visor material are formed of different textured fabric.

16. The reversible hat according to claim 9, wherein the size adjustable portion is attached to a back portion of the main body.

17. The reversible hat according to claim 9, the hat further comprising a sweatband attached to a lower periphery of the inner fabric material.

\* \* \* \* \*